Nov. 23, 1943. E. S. BOERNER Plant Pat. 607
ROSE PLANT
Filed June 26, 1943
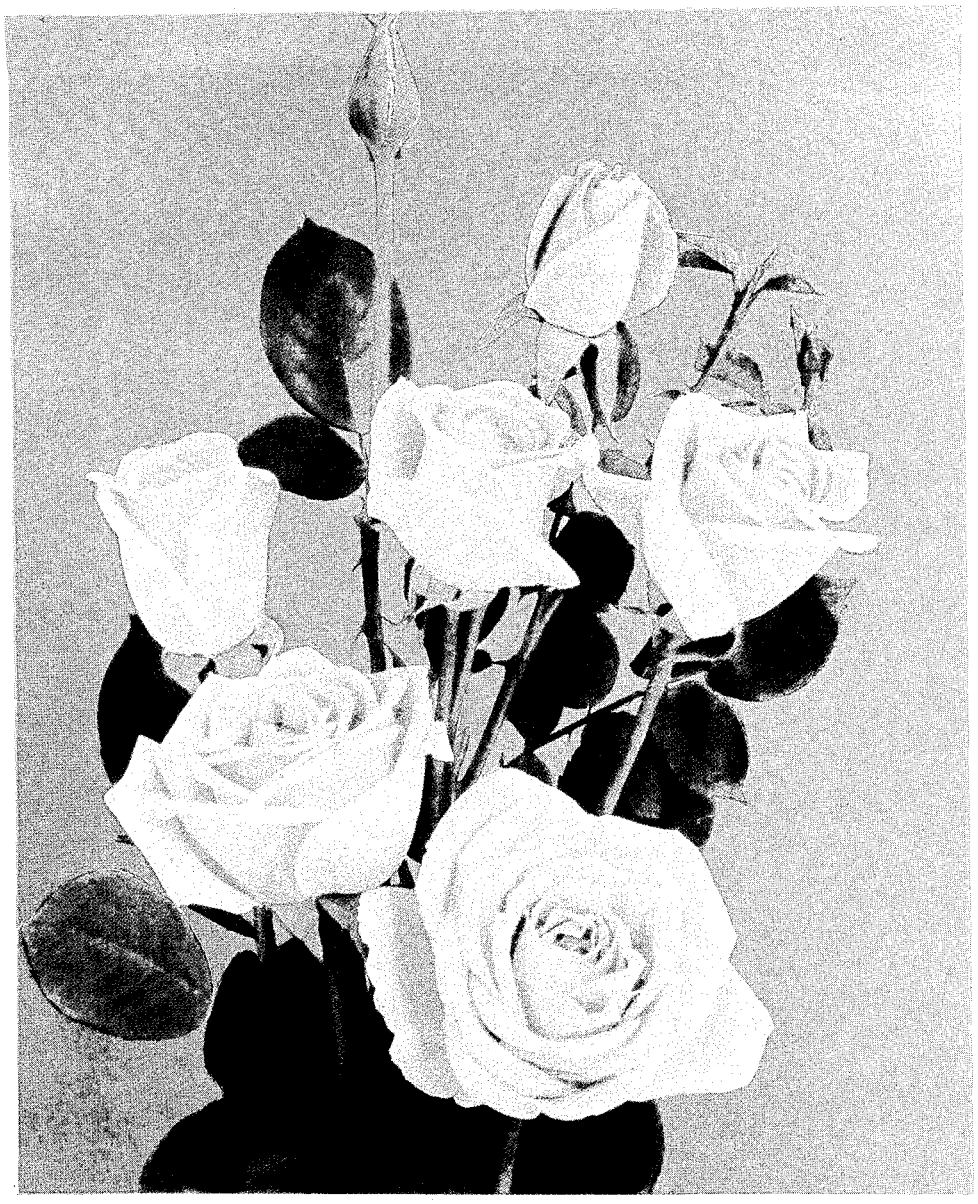
Inventor
E. S. Boerner
By Robb & Robb
Attorneys Patented Nov. 23, 1943

Plant Pat. 607

UNITED STATES PATENT OFFICE

607

ROSE PLANT

Eugene S. Boerner, Newark, N. Y., assignor to Jackson & Perkins Company, Newark, N. Y., a corporation of New York Application June 26, 1943, Serial No. 492,461

1 Claim. (Cl. 47—61)

The present invention relates to a new and distinct variety of rose plant, originated by crossing an unnamed seedling, pink of color and possessing a number of good characteristics, but not quite sufficient for commercial purposes, with the well-known variety "Chieftain."

This new variety constitutes a much improved and commercially desirable rose, characterized as to novelty by its strong, vigorous growth, easily reaching four feet and more, its freedom of blooming equal to or better than the pink Radiance, the pointed bud form and stiff neck, unusual in such a vigorous plant, and the very attractive color combination of the open flower, shown clearly in the accompanying drawing.

Asexual reproduction shows that these characteristics hold true through succeeding propagations.

The following is a detailed description of this new variety, color terminology being in accord with Ridgway's Color Standard:

Parentage: Seedling.

*Seed parent.*—Unnamed, pink of color.

*Pollen parent.*—"Chieftain."

Classification: Botanic and commercial—hybrid tea.

*Flower*

(Observations made in the fields of Jackson & Perkins Company, Newark, New York, in the month of October, 1942.)

Blooming habit: Recurrent—continuous.

Bud:

*Size.*—Large.

*Form.*—Pointed. Is not affected by wet or hot weather.

*Color.*—When sepals first divide—Rose Doree, Plate 1. When petals begin to unfurl—Begonia Rose, Plate 1, with Buff Yellow, Plate 4, at base. When half blown: Inside of petals—Between Deep Rose Pink, Plate 12, and Geranium Pink, Plate 1. Reverse of petals—Eosine Pink, Plate 1, flushed with Buff Yellow, Plate 1, at base.

*Sepals.*—Serrated, branched; curl back when when petals begin to unfurl. Color—Inside—Veronese Green, Plate 18; outside—Lettuce Green, Plate 5.

*Calyx.*—Shape—Apple. Size—broad. Aspect—smooth. Color—Oil Green, Plate 5. Odor when rubbed—none.

*Peduncle.*—Length—long. Aspect—prickly. Color—Oil Green, Plate 5. Strength—erect; slender.

*Opening.*—Opens up well. Is not affected by adverse conditions.

Bloom:

*Size.*—Very large. Average size when fully expanded, 4¾ inches.

*Borne.*—Singly.

*Stems.*—Long; strong.

*Form.*—When first open—high center. Permanence—retains its form to the end.

*Petalage.*—Double (full but open center). Number of petals under normal conditions, 22.

*Color.*—Center of flower—Thulite Pink, Plate 26, shaded with Rose Pink, Plate 12. Outer petals—Rose Pink, Plate 12. Base of petals (aiglet)—Pale Lemon Yellow, Plate 4. Inside of petals—between Thulite Pink, Plate 26, and Rose Pink, Plate 12, overcast with Buff Yellow, Plate 4, in the lower half of the petal. Reverse of petals—Thulite Pink, Plate 26, overcast with Buff Yellow, Plate 4, in lower half of petal. General tonality for a distance—Rose Pink, Plate 12.

*Discoloration.*—General tonality at end of first day—Thulite Pink, Plate 26, shaded with Rose Pink, Plate 12. Second day—between Thulite Pink, Plate 26, and Rose Pink, Plate 12. Third day—Rose Pink, Plate 12.

Petals:

*Texture.*—Thick. Is not affected by wet or hot weather.

*Appearance.*—Inside—shiny. Outside—satiny.

*Form.*—Round; notched.

*Arrangement.*—Imbricated (regularly arranged shinglelike). Petaloids in center, none.

*Persistence.*—Drop off cleanly.

*Fragrance.*—Slight. Nature—Fruity (Russet apple).

*Lasting quality.*—On the plant and as cut flower, long.

Genital organs:

*Stamens, anthers.*—Size—large; many. Color—Orange Buff, Plate 3. Arrangement—regular around styles.

*Stamens, filaments (threads).*—Length—medium. Color—Apricot Yellow, Plate 4.

*Pollen.*—Buff Yellow, Plate 4.

*Styles.*—Bunched, uneven length; medium long; thin.

*Stigmas.*—Maize Yellow, Plate 4.

*Ovaries.*—Some protruding from calyx.

*Plant*

Form: Bush.
Growth: Vigorous; upright.
Foliage: 5–7 leaflets.
*Size.*—Large.
*Quantity.*—Abundant.
*Color.*—New foliage: upper side—Oil Green, Plate 5; serrations and mid-rib, Acajou Red, Plate 13; under side—Light Cress Green, Plate 31, overcast slightly with Acajou Red, Plate 13. Old foliage: upper side—Dark Cress Green, Plate 31; under side—Light Cress Green, Plate 31;
*Shape.*—Oval pointed.
*Texture.*—Upper side—leathery; glossy. Under side—smooth. Ribs and veins—ordinary.
*Edge.*—Serrated (saw toothed).
*Serration.*—Single; large; sharp.
*Rachis.*—Jade Green, Plate 31. Under side—smooth.
*Stipules.*—Medium length; slightly bearded.
*Disease resistance.*—Resistant insofar as this is evidenced by absence of any disease throughout development and establishment of this variety.

Wood:
*New wood.*—Color—Yellowish Oil Green, Plate 5. Bark—smooth.
*Old wood.*—Color—Cerro Green, Plate 5. Bark—smooth.

Thorns (thorns are divided into thorns, prickles and short needles):
*Thorns.*—Quantity—on main stalks from base and on laterals from stalk—ordinary. Form—narrow base; medium length; hooked downward. Color when young—Light Corinthian Red, Plate 27. Position—irregular.
*Prickles.*—Quantity—on main stalks and on laterals, none.
*Short needles.*—Quantity—on main stalks and on laterals, none.

I claim:

A new and distinct variety of Rose plant, characterized as to novelty by its strong, vigorous, high growth; unusual freedom of blooming, pointed form of bud on stiff neck, and attractive color combination of the open flowers, substantially as shown and described.

EUGENE S. BOERNER.